United States Patent
Biagiotti, Jr.

(10) Patent No.: US 7,190,154 B2
(45) Date of Patent: Mar. 13, 2007

(54) METHOD AND SYSTEM FOR MEASURING A CONDITION OF A STRUCTURE

(75) Inventor: Stephen Francis Biagiotti, Jr., The Woodlands, TX (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 10/908,890

(22) Filed: May 31, 2005

(65) Prior Publication Data
US 2006/0267569 A1  Nov. 30, 2006

(51) Int. Cl.
*G01N 27/00* (2006.01)
(52) U.S. Cl. .................................... 324/71.1
(58) Field of Classification Search .............. 324/71.1
See application file for complete search history.

(56) References Cited

U.S. PATENT DOCUMENTS

| | | | | |
|---|---|---|---|---|
| 4,228,399 A | * | 10/1980 | Rizzo et al. | 324/522 |
| 5,156,042 A | * | 10/1992 | Carlin et al. | 73/49.2 |
| 5,565,633 A | * | 10/1996 | Wernicke | 73/865.8 |
| 5,747,983 A | | 5/1998 | Lara et al. | 324/71.1 |
| 5,999,107 A | | 12/1999 | Cooper et al. | 340/870.16 |
| 6,060,877 A | * | 5/2000 | Nekoksa | 324/71.1 |
| 6,715,370 B2 | * | 4/2004 | Tasca | 73/865.8 |
| 6,870,356 B2 | * | 3/2005 | Murray et al. | 324/71.1 |
| 2003/0074162 A1 | * | 4/2003 | Fourie et al. | 702/188 |

* cited by examiner

*Primary Examiner*—Andrew H. Hirshfeld
*Assistant Examiner*—Timothy J. Dole
(74) *Attorney, Agent, or Firm*—Cantor Colburn LLP

(57) ABSTRACT

A method for measuring a condition of a structure including: moving a measurement probe through a tunnel and measuring the condition of the structure with the measurement probe wherein the tunnel is in electrical potential measurement proximity to the structure.

19 Claims, 3 Drawing Sheets

METHOD AND SYSTEM FOR MEASURING A CONDITION OF A STRUCTURE

BACKGROUND

This disclosure relates to testing and evaluating cathodic protection effectiveness on buried or submerged metallic structures, and specifically to the evaluation of corrosion protection levels on pipelines, tanks, piles, and piping systems.

Buried or submerged metallic structures, such as pipelines, tanks, and distribution piping systems are usually coated with non-conductive material to prevent corrosion. If any corrosion occurs in any uncoated areas of the structure adverse effects may occur which will reduce the effective life of the structure. To prevent such adverse effects, most pipelines are provided with corrosion protection comprising cathodic protection, in addition to the non-conductive coating. Cathodic protection provides corrosion protection to any bare metal areas exposed to soil due to coating defects, by causing direct current to flow from the soil into the structure, thereby polarizing the structure as a cathode. The required direct current output of the cathodic protection system is reduced to manageable levels by the coating, which substantially reduces the bare metal area of the structure exposed to soil.

The objective of the cathodic protection is to shift the potential of the structure to a more negative potential. The potential shift must be large enough to mitigate structure corrosion. Potential criteria have been developed by the National Association of Corrosion Engineers (RP0169-92) to provide guidance for determination of safe cathodic protection levels to mitigate corrosion. One of the criteria is based on a single value of potential, measured with a regular high-impedance voltmeter with the cathodic protection system operating. The potential measured with the cathodic protection system operating are identified as "on" potential readings. This measurement is very easy to take, however, it requires a consideration or elimination of voltage drops in resistive materials between the reference electrode and the structure. Another criterion is based on achieving the same value of structure potential immediately after interrupting the operation of the cathodic protection system, and is referred to as an "off" potential reading. A further criterion is based on a single value of the structure potential decay, which is measured from the "off" potential, leaving the cathodic protection system disconnected for several hours or days.

There is no easy and practical method to determine the voltage drop when the "on" potential reading is taken. Therefore, the "off" potential readings, which eliminate the soil voltage drop measured immediately after interrupting the cathodic protection system from the structure, are often used for monitoring corrosion protection levels. However, the "off" potential readings are much more difficult to take than the "on" readings. The interpretation of the "off" potential readings is also much more complex. The "off" potential readings often require use of synchronized current interrupters, fast reacting recorders, oscilloscopes, or wave analyzers. The "off" potential readings after cathodic protection is interrupted can be adversely affected by long-cell currents in the structure caused by currents flowing between more polarized sections of the structure being protected, which occur in the proximity of the rectifiers, and less polarized sections of the structure being protected, which typically occur at sections of the structure that are generally equidistant between sequential rectifiers. Also, the "off" potential readings are often adversely affected by inductive or capacitive voltage spikes, caused by cathodic protection interruption. If the "off" potential reading is taken some time after the spike, some of the polarization is lost and the reading could be therefore invalid.

Meeting the "off" potential criterion often requires that more cathodic protection current be applied than is required to meet the "on" potential criterion, resulting in possible overprotecting of the structure, faster deterioration of the coating, and a higher probability of hydrogen evolution and steel embrittlement within the structure. The "off" potential measurements are not valid in areas where substantial uninterruptable direct currents are flowing through the soil into or from the structure, polarizing the structure. Such conditions exist, for instance in stray current areas, where the structure is affected by stray currents from electric railroads, from cathodic protection systems on foreign structures, and in areas with telluric (earth) currents naturally induced by fluctuations in the earth's magnetic field. Also, the "off" potential readings cannot be used on structures with distributed galvanic anodes directly connected to the structure.

To eliminate some of the disadvantages of the "off" potential readings on the structure, different cathodic protection test probes and coupon/access tube assemblies have been proposed. The probes consist of a short steel pipe section as a coupon, a plastic tube filled with conductive backfill functioning as an electrolytic "salt bridge," and a porous ceramic plug glued to the end of the plastic tube, representing a potential sensing area. A coupon is a metal electrode, which simulates an area in which the non-conductive coating is not present on the structure and provides a reference from which the cathodic protection system can be measured. Coupons are made from the same or similar metal as the structure, and are electrically connected to the structure to receive cathodic protection. Cathodic protection probes with cylindrical coupons, now commercially available, have been described in Material Performance, published by National Association of Corrosion Engineers, Houston, Tex., June 1996, pp. 21–24.

Cathodic protection probes with cylindrical coupons are difficult to use when the structure to be tested is located beneath a surface obstruction that prevents access to the soil from the ground surface without interactions with the surface obstruction. Conducting periodic inspections of structures located beneath surface obstructions, such as paved surfaces, using currently available methods is costly and destructive.

SUMMARY

Embodiments of the invention include a method for measuring a condition of a structure including: moving a measurement probe through a tunnel and measuring the condition of the structure with the measurement probe wherein the tunnel is in electrical potential measurement proximity to the structure.

Embodiments of the invention also include a system for measuring a condition of a structure including: a tunnel in electrical potential measurement proximity to the structure; a measurement probe receivable inside the tunnel; and a movement system operable for moving the measurement probe through the tunnel wherein said measurement probe measures one or more conditions of the structure.

Further embodiments of the invention include a system for measuring a condition of a structure including: means for moving a measurement probe through a tunnel, wherein the tunnel is in electrical potential measurement proximity to the structure; and means for measuring the condition of the structure using known electrical techniques.

BRIEF DESCRIPTION OF THE DRAWINGS

These and other features, aspects, and advantages of the present invention will become better understood when the following detailed description is read with reference to the accompanying figures, wherein.

DETAILED DESCRIPTION

Figure 1:
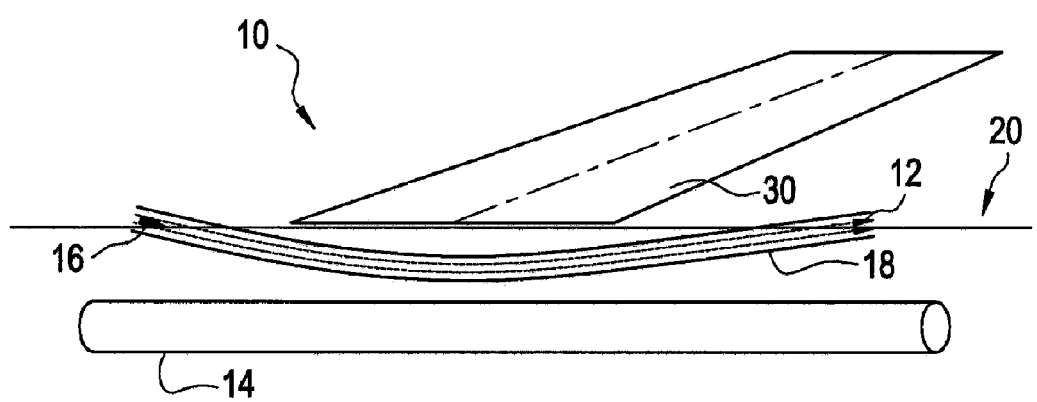
FIG. 1 depicts an exemplary embodiment of a system for measuring the condition of a structure.

Illustrated in FIG. 1 is an exemplary embodiment of a system for measuring a condition of a structure 10. In one embodiment, which is illustrated in FIG. 1, the system for measuring the condition of the structure 10 includes a support device, which in this embodiment is illustrated as a conduit 12, in electrical potential measurement proximity to a structure, which in this embodiment is illustrated as a pipeline 14, and a measurement probe 16 designed to fit inside the conduit 12. The system for measuring a condition of a structure 10 also includes a tunnel 18 that is created, and may be excavated, using commonly known methods including directional drilling techniques. The tunnel 18 is separate from the pipeline 14 as shown in FIG. 1, and may be any opening suitable to allow use of the probe described herein. After creation of the tunnel 18, the conduit 12 is positioned inside of the tunnel 18. The measurement probe 16 may be inserted into the conduit 12 at any time. After insertion into the conduit 12, the measurement probe 16 is moved through the conduit 12. As the measurement probe 16 traverses the conduit 12, measurements of the conditions of the structure, such as cathodic protection potentials, are taken at specified intervals. In an exemplary embodiment, the measurement probe 16 may be a corrosion measurement half-cell, which generally is any device that contains an electrode and a surrounding electrolyte, and the conduit 12 maybe a plastic conduit or any other conduit that is constructed of a suitable electrically permeable membrane.

The conduit 12 may be pulled or pushed through the tunnel 18 such that either or both ends of the conduit 12 are exposed above the ground surface 20 or at least located to allow for easy access to the conduit 12. In an exemplary embodiment, the exposed ends of the conduit 12 are fitted with removable end caps to facilitate periodic inspections. Optionally, the conduit 12 can be filled with water and the measurement probe 16 will be pulled or pushed through the conduit 12. The conduit 12 ensures that tunnel 18 will remain intact to allow for periodic inspections without destruction or interference with the surface obstructions 30.

In another exemplary embodiment, the system for measuring a condition of a structure 10 includes the measurement probe 16 and the tunnel 18 in electrical potential measurement proximity to a structure, such as the pipeline 14. After creation of the tunnel 18, the measurement probe 16 may be inserted into and moved through the tunnel 18. While moving through the tunnel 18 the measurement probe 16 takes measurements of the conditions of the structure. Optionally, a support device may be positioned in the tunnel 18 to maintain the structural integrity of the tunnel 18 after it is created, thereby facilitating periodic inspections.

In an alternative exemplary embodiment, the system for measuring a condition of a structure 10 includes the measurement probe 16 that is coupled to an excavation tool. The excavation tool is used to create the tunnel 18 in electrical potential measurement proximity to a structure, such as the pipeline 14. After creation of tunnel 18 the measurement probe 16 and coupled excavation tool are retracted through tunnel 18. The measurement probe 16 may take measurements of the condition of the structure either during creation of the tunnel 18 or during retraction of the measurement probe 16.

Figure 2:
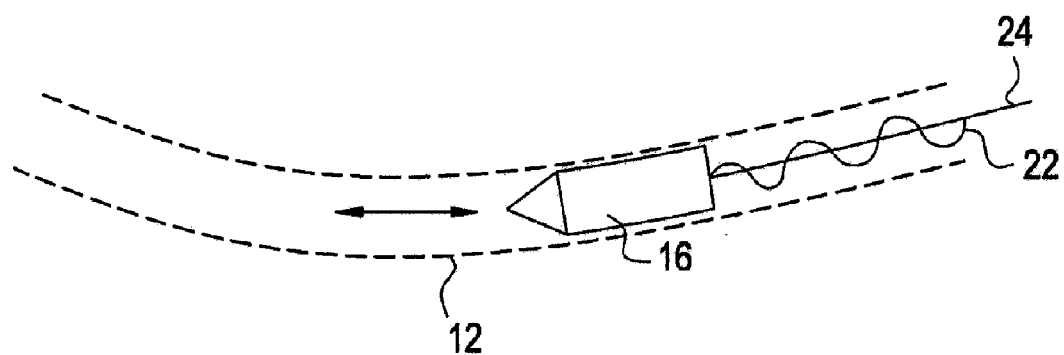
FIG. 2 depicts an exemplary embodiment of a system for measuring a condition of a structure where a measurement probe is shown inside the conduit.

FIG. 2 depicts an exemplary embodiment of a system for measuring a condition of a structure 10 where the measurement probe 16 is shown inside the conduit 12. The measurement probe 16 may be connected to a measurement device located above the ground surface 20 by a measurement wire 22. The measurement wire 22 communicates the properties measured by the measurement probe 16 to the measurement device. A tether cable 24 will also be connected to the measurement probe 16 which will facilitate retracting the measurement probe 16 through the conduit 12. Additionally, the tether cable 24 allows an operator to retrieve the measurement probe 16 in the event that the measurement probe 16 becomes stuck in the conduit 12.

After being inserted into the conduit 12 the measurement probe 16 will be moved through the conduit 12 using any suitable movement means including, but not limited to, gas or liquid propulsion. In an exemplary embodiment, the measurement probe 16 is moved through the conduit 12 by a movement system that employs any suitable form of propulsion. The measurement probe 16 is then retracted through the conduit 12 at a controlled rate using the tether cable 24. The measurement probe 16 measures the condition of the pipeline 14 at specific intervals while it is being retracted. In another exemplary embodiment, the measurement probe 16 is moved through the conduit 12 by a movement system that employs any suitable form of propulsion and the measurement probe 16 measures the condition of the pipeline 14 while it is being moved through the conduit 12. In an alternative exemplary embodiment, the measurement probe 16 is moved through the conduit 12 at a controlled rate and the measurement probe 16 measures the condition of the pipeline 14 while it is being moved through the conduit 12. In yet another exemplary embodiment, the measurement probe 16 is self-motivated and moves through the conduit 12 while measuring the condition of the pipeline 14.

Figure 3:
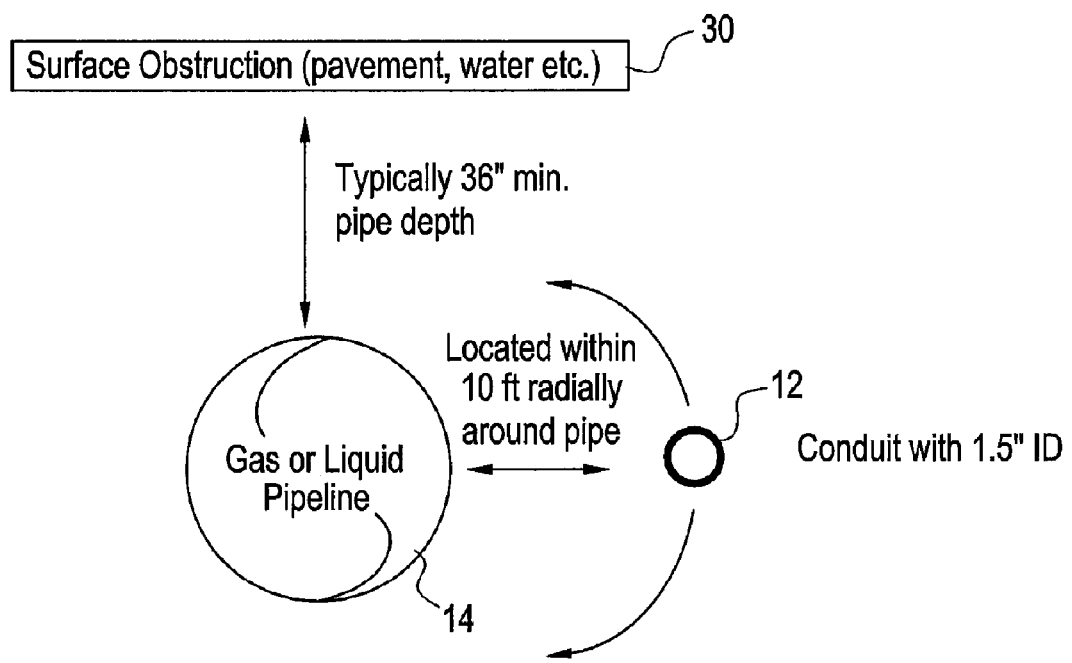
FIG. 3 depicts another exemplary embodiment of a system for measuring the condition of a structure.

Turning now to FIG. 3, which depicts another exemplary embodiment of the system for measuring the condition of the structure 10 where the structure shown is the pipeline 14, which is located at typically three feet below the surface obstruction 30. As shown in FIG. 3, the tunnel 18 should be created such that the conduit 12, once inserted in the tunnel 18, is located approximately within ten feet radially from the pipeline 14. Additionally, the tunnel 18 should be created such that the conduit 12, once inserted in the tunnel 18, is approximately parallel to the pipeline 14. The proper positioning of the tunnel 18 with respect to the pipeline 14 ensures that the measurement probe 16 is able to take accurate measurements of the condition of the pipeline 14.

In an exemplary embodiment, the condition of a pipeline 14, specifically the presence of external corrosion, is indirectly measured with a measurement probe 16 using known electrical techniques. Before measuring the condition of the pipeline 14, a tunnel 18 is created in electrical potential measurement proximity to the pipeline 14 to be inspected, in one embodiment, within 10 feet radially. After creating the tunnel 18, a conduit 12 constructed of any suitable electrically permeable material is inserted into the tunnel 18. The conduit 12 may be inserted such that one or both ends of the conduit 12 remain above the ground surface 20, or at least located to allow for easy access to the conduit 12, to facilitate periodic inspections. Optionally, the exposed ends of the conduit 12 may be fitted with removable end caps. After the conduit 12 has been inserted into the tunnel 18, a measurement probe 16 is inserted in one end of the conduit 12 and is moved through the conduit 12 using any suitable movement means including, but not limited to, liquid or gas propulsion. In an alternative exemplary embodiment, the measurement probe 16 is self-motivated.

The measurement probe 16 may be connected to a measurement device located above the ground surface 20 by a measurement wire 22. The measurement wire 22 is used to communicate measured values from the measurement probe 16 to the measurement device. Additionally, the measurement probe 16 may be attached to a tether cable 24 that facilitates retracting and removing the measurement probe 16 from the conduit 12. The measurement probe 16 may take measurements of the condition of the pipeline 14 continuously or at specific intervals either while being moved through the conduit 12 or while being retracted through the conduit 12. In an alternative exemplary embodiment, the measurement probe 16 may include a data storage device to record the values that the measurement probe 16 reads from pipeline 14.

The system for measuring a condition of a structure 10 greatly increases the efficiency of periodically testing the conditions of a structure, such as the pipeline 14. Once the system for measuring a condition of a structure 10 has been used to measure the condition of a specific pipeline 14, the conduit 12 may be sealed with one or more removable end caps. Subsequent inspections of the pipeline 14 can be preformed by removing the end caps from the conduit 12, placing the measurement probe 16 into the conduit 12, moving the measurement probe 16 through the conduit 12, measuring the condition of the pipeline 14, and retracting the measurement probe 16 through the conduit 12. This process will reduce the time required for subsequent inspections and will eliminate disturbance of surface structures.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for measuring a condition of a structure comprising:
   removing an end cap to access a tunnel;
   inserting a measurement probe into said tunnel;
   moving said measurement probe into said tunnel;
   measuring the condition of the structure with said measurement probe; and
   replacing said end cap wherein said tunnel is separate from the structure but in electrical potential measurement proximity to the structure and said tunnel includes a support device to maintain the structural integrity of said tunnel and the structure is beneath a surface obstruction.

2. The method of claim 1 wherein the condition of the structure comprises a cathodic protection potential.

3. The method of claim 1 wherein said tunnel is approximately parallel to the structure.

4. The method of claim 1 wherein said support device is a conduit disposed in said tunnel.

5. The method of claim 4 further comprising removing said measurement probe from said tunnel and placing one or more removable end caps on one or more ends of said conduit.

6. The method of claim 1 further comprising retracting said measurement probe through said tunnel with a tether cable attached to said measurement probe.

7. The method of claim 1 wherein said measuring the condition of the structure with said measurement probe occurs repeatedly at specified intervals.

8. The method of claim 1 wherein said measuring the condition of the structure with said measurement probe occurs continuously while moving said measurement probe within said tunnel.

9. A system for measuring a condition of a structure comprising:
   a tunnel separate from the structure but in electrical potential measurement proximity to the structure which lies beneath a surface obstruction;
   a support device disposed inside said tunnel;
   a removable end cap operative for sealing said tunnel;
   a measurement probe receivable inside said tunnel; and
   a movement system operable for moving said measurement probe into said tunnel wherein said measurement probe measures one or more conditions of the structure.

10. The system of claim 9 wherein said support device is constructed of an electrically permeable material and maintains structural integrity of said tunnel.

11. The system of claim 10 wherein said support device is a conduit.

12. The system of claim 11 wherein the removable end cap is designed to fit an end of said conduit wherein said removable end caps facilitate periodic inspections.

13. The system of claim 9 wherein said measurement probe is a corrosion half-cell.

14. The system of claim 9 further comprising a tether cable attached to said measurement probe wherein said tether cable facilitates positioning and retracting said measurement probe through said tunnel.

15. The system of claim 9 further comprising a measurement device and a measurement wire wherein said measurement probe is attached to said measurement device by said measurement wire.

16. The system of claim 9 wherein the condition of the structure comprises a cathodic protection potential.

17. A system for measuring a condition of a structure comprising:
   means for maintaining structural integrity of a tunnel;
   means for sealing said tunnel;
   means for moving a measurement probe through said tunnel, wherein said tunnel is separate from said structure, but in electrical potential measurement proximity to the structure; and
   means for measuring the condition of the structure using known electrical techniques.

18. The system of claim 17 wherein the condition of the structure comprises a cathodic protection potential.

19. The system of claim 17 further comprising means for retracting said measurement probe through said tunnel.

* * * * *